US009857389B2

(12) United States Patent
Endo et al.

(10) Patent No.: US 9,857,389 B2
(45) Date of Patent: Jan. 2, 2018

(54) SPECIMEN STORAGE APPARATUS, SPECIMEN PROCESSING SYSTEM, AND CONTROLLING METHOD THEREOF

(71) Applicant: Hitachi High-Technologies Corporation, Tokyo (JP)

(72) Inventors: Masashi Endo, Tokyo (JP); Tatsuya Fukugaki, Tokyo (JP); Yoshiteru Hirama, Tokyo (JP); Kazuma Tamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 155 days.

(21) Appl. No.: 14/423,473

(22) PCT Filed: Aug. 28, 2013

(86) PCT No.: PCT/JP2013/073046
§ 371 (c)(1),
(2) Date: Feb. 24, 2015

(87) PCT Pub. No.: WO2014/042011
PCT Pub. Date: Mar. 20, 2014

(65) Prior Publication Data
US 2016/0202279 A1    Jul. 14, 2016

(30) Foreign Application Priority Data

Sep. 12, 2012   (JP) .................................. 2012-200068
Sep. 28, 2012   (JP) .................................. 2012-215459

(51) Int. Cl.
*G01N 35/02*     (2006.01)
*G01N 35/00*     (2006.01)
*G01N 35/04*     (2006.01)

(52) U.S. Cl.
CPC ..... *G01N 35/028* (2013.01); *G01N 35/00584* (2013.01); *G01N 35/00603* (2013.01);
(Continued)

(58) Field of Classification Search
None
See application file for complete search history.

(56) References Cited

U.S. PATENT DOCUMENTS 5,233,844  A      8/1993   Knippscheer et al.
2007/0071645  A1   3/2007   Araki
(Continued)

FOREIGN PATENT DOCUMENTS

GB    EP 1634496 A1 *  3/2006  ............... A01N 1/02
JP           63-317773 A    12/1988
(Continued)

OTHER PUBLICATIONS

Japanese Office Action received in corresponding Japanese Application No. 2014-535481 dated Aug. 2, 2016.
(Continued)

*Primary Examiner* — P. Kathryn Wright
(74) *Attorney, Agent, or Firm* — Mattingly & Malur, PC

(57) ABSTRACT

The specimen storage apparatus includes: a specimen conveyor line which conveys a specimen for which the pre-processing is completed and which is installed on a specimen conveyance holder; a lift mechanism capable of driving a specimen tray having the specimen installed therein in front-and-back and vertical directions; a specimen chuck mechanism which transfers the specimen from a specimen acquisition position of the specimen conveyor line to the specimen tray on the lift mechanism; a specimen storage unit which receives the specimen tray from the lift mechanism, includes hierarchical specimen storage spaces in a vertical direction, and accommodates a plurality of speci-
(Continued)

men trays in a lateral direction while keeping them cold; a shutter mechanism which is opened and closed at the time of delivery of the specimen tray between the lift mechanism and the specimen storage unit; and a control unit which controls each of the mechanisms.

14 Claims, 10 Drawing Sheets

(52) U.S. Cl.
CPC ......... *G01N 35/04* (2013.01); *G01N 35/0099* (2013.01); *G01N 2035/00346* (2013.01); *G01N 2035/00445* (2013.01); *G01N 2035/041* (2013.01); *G01N 2035/0425* (2013.01); *G01N 2035/0462* (2013.01); *G01N 2035/0465* (2013.01)

(56) References Cited

U.S. PATENT DOCUMENTS

| | | |
|---|---|---|
| 2008/0041956 A1 | 2/2008 | Neeper et al. |
| 2008/0226498 A1 | 9/2008 | Stylli et al. |
| 2009/0003981 A1 | 1/2009 | Miller |
| 2012/0036944 A1* | 2/2012 | Chida .............. G01N 35/00613 73/863.01 |
| 2012/0321419 A1* | 12/2012 | Neeper ............ G01N 35/00732 414/281 |
| 2013/0061693 A1 | 3/2013 | Sasaki et al. |

FOREIGN PATENT DOCUMENTS

| | | |
|---|---|---|
| JP | 6-509782 A | 11/1994 |
| JP | 09043246 | 2/1997 |
| JP | 2001-124786 A | 5/2001 |
| JP | 2007089416 | 4/2007 |
| JP | 2007309675 | 11/2007 |
| JP | 2012021911 | 2/2012 |
| WO | 2011148897 | 12/2011 |

OTHER PUBLICATIONS

International Search Report in PCT/JP2013/073046, dated Sep. 24, 2013.

Extended European Search Report received in corresponding European Application No. 13837351.9 dated May 3, 2016.

* cited by examiner

FIG. 3
(a)
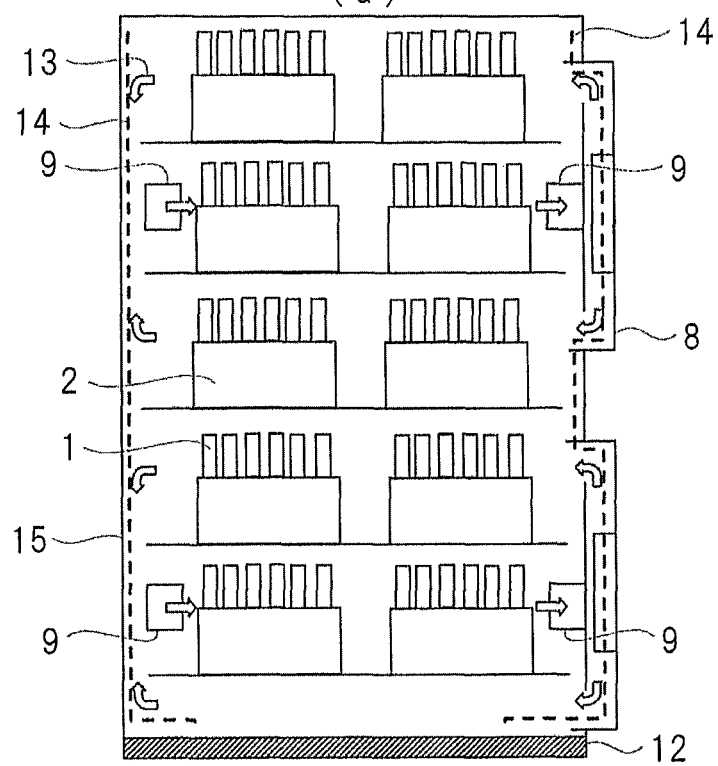
(b)
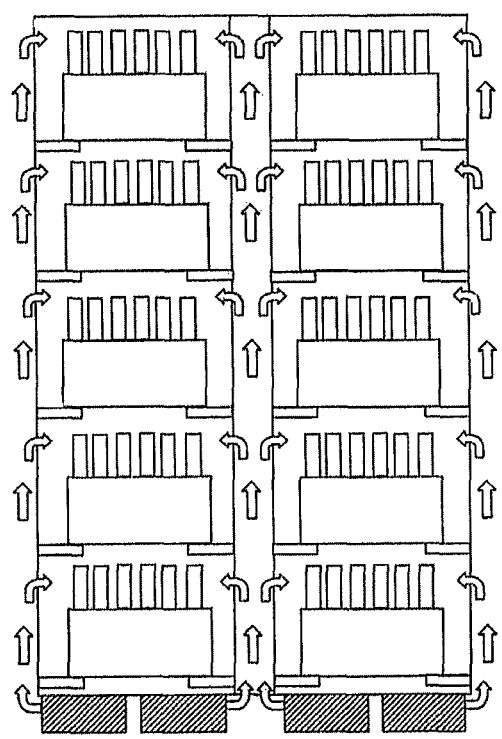

FIG. 4
(a)
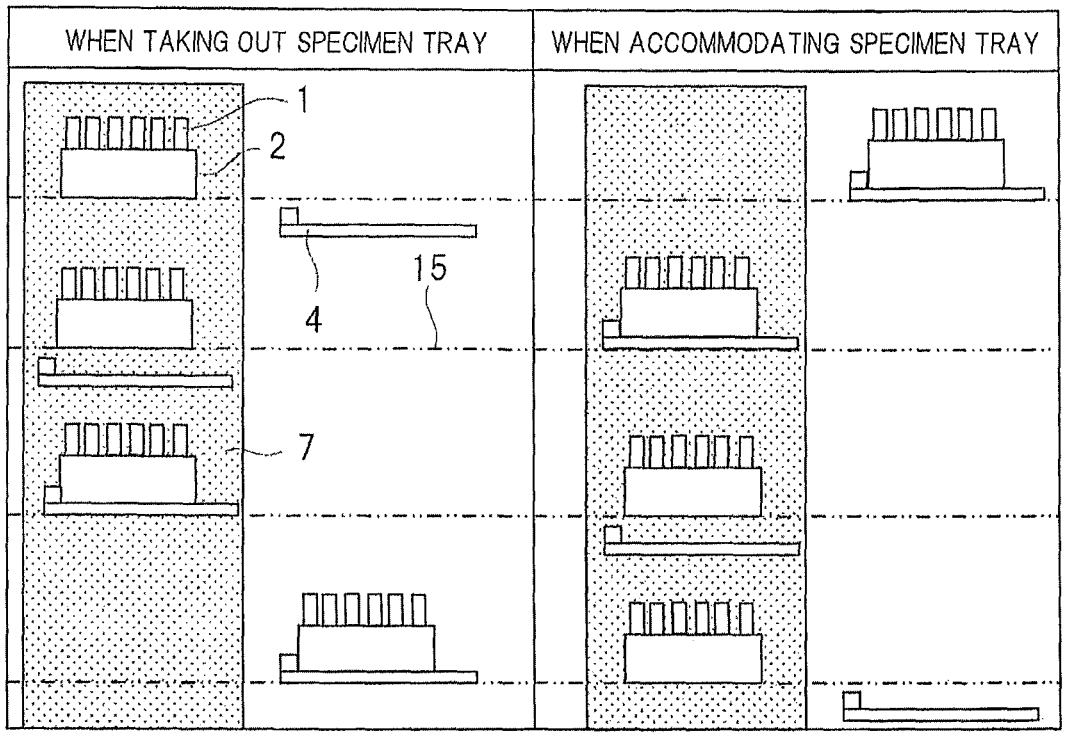
(b)
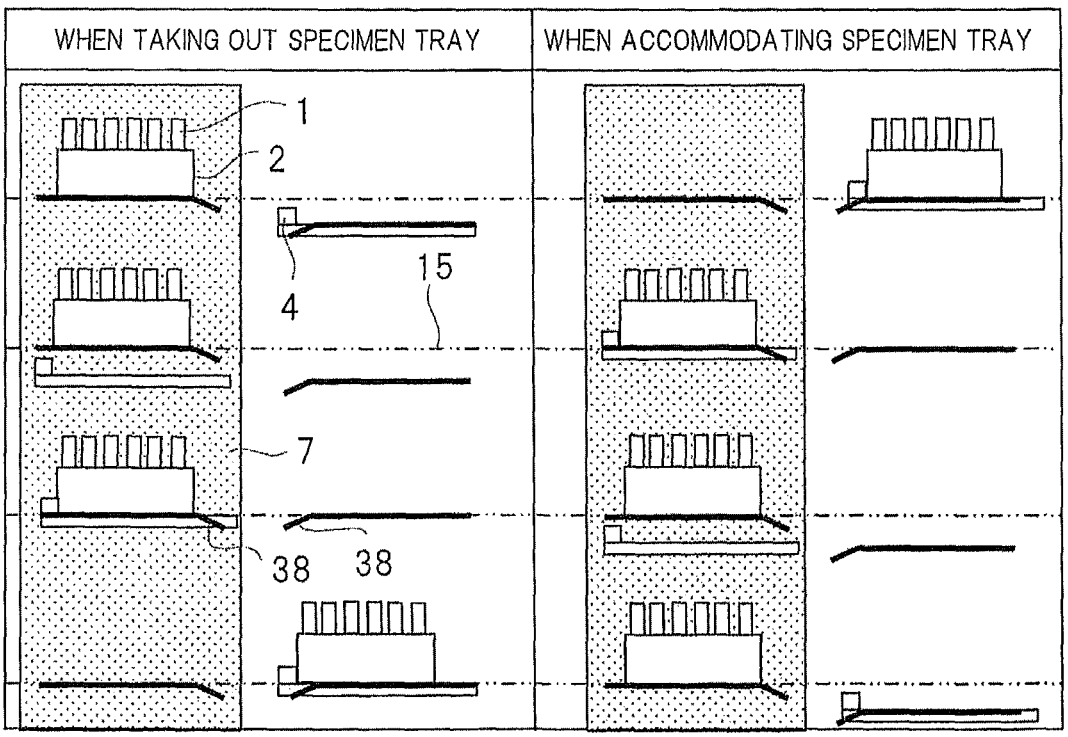

FIG. 8
(a) (b)
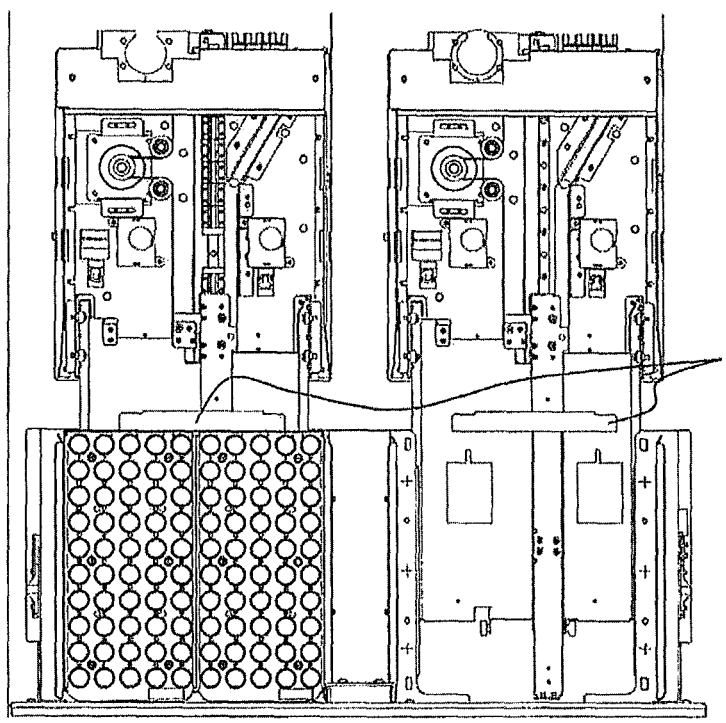
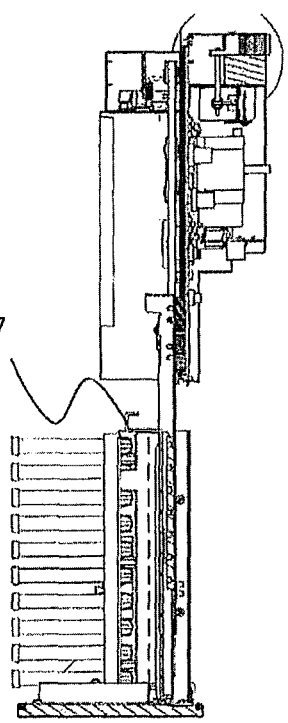
17

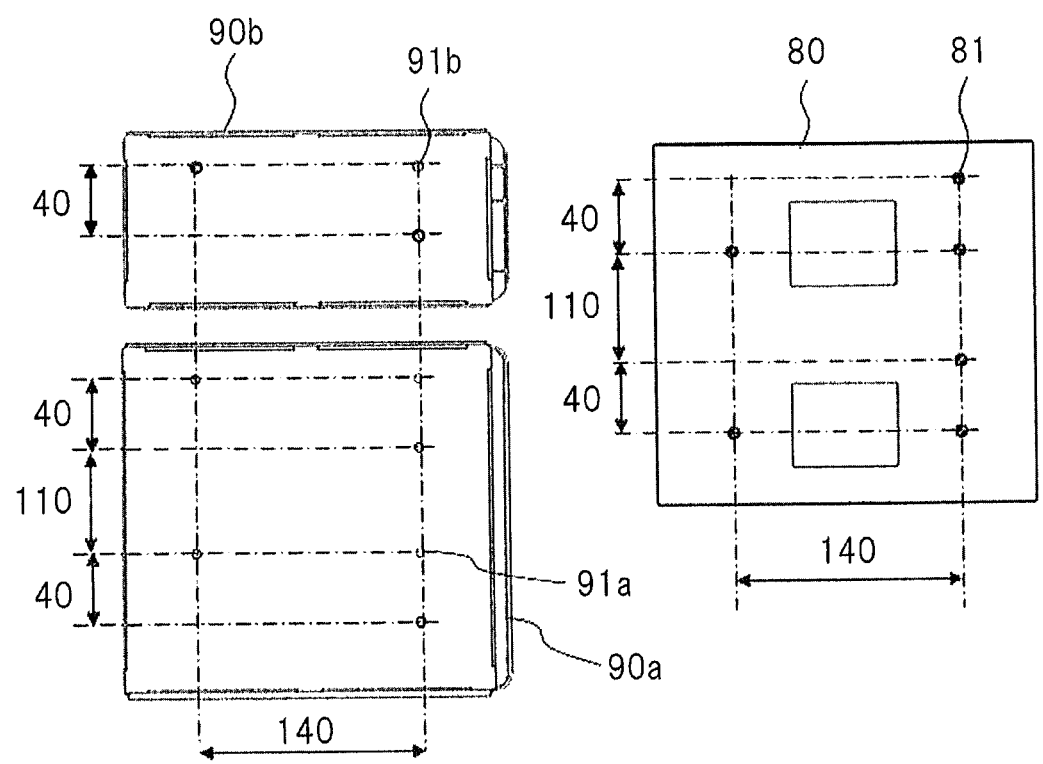

SPECIMEN STORAGE APPARATUS, SPECIMEN PROCESSING SYSTEM, AND CONTROLLING METHOD THEREOF

TECHNICAL FIELD

The present invention relates to a specimen storage apparatus which stores a parent test tube and a preserved child specimen after pre-processing and analysis processing and a system including the specimen storage apparatus.

BACKGROUND ART

In the field of clinical test, a specimen such as blood or urine taken from a patient at a hospital is enclosed in a test tube, is delivered to a laboratory in the hospital or a test center, and is analyzed by an analyzing apparatus. When the specimen is loaded into the analyzing apparatus, various kinds of pre-processing such as centrifugation for the test tube in which the specimen is enclosed (hereinafter, referred to as a parent specimen test tube), plug opening of parent specimen test tube, preparation of a plurality of test tubes (hereinafter, referred to as child specimen test tubes) used at the time of dispensing a specimen from the parent specimen test tube, and dispensing of a child specimen are performed, and then the specimen is delivered to the analyzing apparatus for analysis processing. When a request for a retest based on the test result is not made, the specimen for which the analysis is completed is conveyed to a storage module and accommodated and stored therein.

In recent years, a series of these operations regarding pre-processing, conveyance to the analyzing apparatus, analysis, and specimen storage after analysis have been automated and used as a specimen pre-processing system or specimen conveyor system in a laboratory in the hospital or a test center.

Patent Document 1 discloses a system in which a specimen is loaded and analyzed and then the analyzed specimen is stored, and the system includes a rack collecting apparatus which accommodates racks holding the analyzed specimens in trays and arranges the trays vertically in five stages and laterally in two columns for storage.

Also, when storing the specimens, test tubes containing specimens are mounted on a specimen tray (hereinafter, referred to as a tray) capable of carrying a plurality of test tubes and the tray is stored in a place for cold storage such as a refrigerator. Most operators manage the specimens in units of trays.

Also in a storage apparatus of a specimen test system, a tray used for the specimen storage can be accommodated by directly setting it. This eliminates an interchanging operation of taking out test tubes from a tray and putting them into another storage container at the time of storage and can save trouble. However, the tray is required to have a shape that can be set into the apparatus, and a dedicated tray is used. Since the tray is a dedicated one, the number of test tubes that can be mounted on one tray is fixed, and it is therefore not possible to handle the storage in small quantity and the storage of the test tubes more than the upper-limit number of specimens that can be mounted on the tray.

Also, in a specimen test automation system, a specimen is conveyed via a conveyor line. For example, Patent Document 3 discloses a specimen test automation system in which a specimen conveyed via a conveyor line to a storage apparatus is transferred from the line by a robot arm onto a tray set at a transfer position.

Furthermore, for example, Patent Document 1 discloses a system in which a storage unit for storing a tray is configured in multiple stages and a tray is taken out from any shelf to transfer a specimen at a transfer position.

RELATED ART DOCUMENTS

Patent Documents

Patent Document 1: Japanese Patent Application Laid-Open Publication No. 2007-309675
Patent Document 2: U.S. Pat. No. 5,233,844
Patent Document 3: International Publication No. 2011/148897

SUMMARY OF THE INVENTION

Problems to be Solved by the Invention

In the rack collecting apparatus of Patent Document 1, since the number of specimens that can be stored is about five hundreds and the specimen storage apparatus does not have the cold storage function, if many specimens have been processed or the specimen is required to be preserved for a long period of time, an operator needs to perform the task of transferring the tray to a refrigerator. In the case of this operation, when a request for a retest or additional test is made after the specimen is stored in the refrigerator, the operator is required to visually search the refrigerator for the relevant specimen and load the specimen to the apparatus again.

Patent Document 2 discloses a specimen storage chamber with a cold storage function. In the description of this apparatus, a storage apparatus can store a specimen while keeping it cold in a storage, and a plurality of trays are configured in multiple stages in this storage apparatus and each tray can be vertically driven. However, Patent Document 2 does not describe that a specimen is taken out for a retest from a tray which has been once accommodated and is automatically conveyed to an analyzing apparatus. Therefore, when a request for a retest on the specimen is made after it is stored in the storage apparatus, an operator is required to visually check the tray to search for a relevant specimen and manually take out and load it to the apparatus.

The present invention has been made in view of the above problems, and the first object thereof is to provide a specimen storage apparatus capable of expanding the number of specimens that can be stored for a relatively long period of time and capable of automatically performing a retest when a request for the retest or additional test on the stored specimen is made.

Also, in the specimen test automation system disclosed in Patent Document 3, the storage apparatus does not include a cooling function and cannot store a large number of specimens, for example, several thousands of specimens. For this reason, the operator is required to manually take out a tray from the storage apparatus every time the tray is full and move specimens to an apparatus capable of cold storage such as a refrigerator.

In the system disclosed in Patent Document 1, an operation of taking in and out a tray storing a specimen from a storage unit to a transfer position is required. It is presumable that the control for the operation like this can be achieved by, for example, moving a drawing table from the transfer position to the storage unit by a driving system, inserting the drawing table into a lower side of the tray, directly raising the drawing table to lift the tray, and then returning the drawing table to the transfer position.

When performing the control for the operation like this, the entire surface of the drawing table needs to support a wide area of the bottom surface of the tray so that the drawing table can safely move the tray without dropping off. Specifically, it is presumable that a shelf to which a tray is to be set in the storage unit is configured to have a U shape or the like so as to hold the periphery of the tray and allow the drawing table to access the center part of the tray. In this case, due to the absence of a part for supporting the center part of the tray, there is a danger that the operator may drop the tray by mistake when installing and taking out the tray and the operator may also install the tray in a wrong front-and-back direction.

Furthermore, since a dedicated tray in conformity to the shape of the specimen storage apparatus is conventionally used, the number of test tubes that can be mounted on one tray is fixed, and it is therefore not possible to handle the storage in small quantity and the storage of the test tubes more than the upper-limit number of specimens that can be mounted on the tray.

The present invention has been made in view of the above problems, and the second object thereof is to provide a specimen storage apparatus capable of automatically taking in and out a tray without the danger of dropping of the tray by an operator.

Means for Solving the Problems

To solve the above-described problems, the present invention has the following features.

Namely, as the first aspect, a specimen storage apparatus of the present invention includes: a specimen storage unit in which accommodation positions where trays holding a plurality of specimens can be accommodated are configured in multiple stages; a standby position where a plurality of trays holding the specimens are on standby; at least two transfer means capable of individually transferring a plurality of trays at the standby position; and control means which controls an operation of each of the mechanisms, and the transfer means can individually transfer the plurality of trays between the accommodation positions and the standby position.

Also, as the second aspect, a specimen storage apparatus of the present invention includes: a specimen tray having a plurality of test tube insertion holes for installing the specimens; a specimen holding mechanism which holds the specimen installed on the specimen tray; a tray transfer unit which holds the specimen tray at a position where the specimen holding mechanism installs the specimen; a tray storing unit which stores the specimen installed on the specimen tray while keeping it cold; and a delivering mechanism which delivers the specimen tray between the tray transfer unit and the tray storing unit, and the delivering mechanism takes in and out the tray integrally with a tray installation cassette having the specimen tray mounted thereon.

Effects of the Invention

As a first effect, according to the present invention, it is possible to provide a specimen storage apparatus which can preserve specimens for a long period of time and can automatically make an analysis even when a request for a retest or additional test on a stored specimen is made.

As a second effect, according to the present invention, when the operator takes in and out a tray to and from the specimen storage apparatus, the tray is attached to and detached from the cassette, and when a tray is taken in and out on an apparatus side, the tray is taken in and out integrally with the cassette. Therefore, a tray can be automatically taken in and out without the danger of dropping of the tray by an operator.

BRIEF DESCRIPTIONS OF THE DRAWINGS

Figure 5:
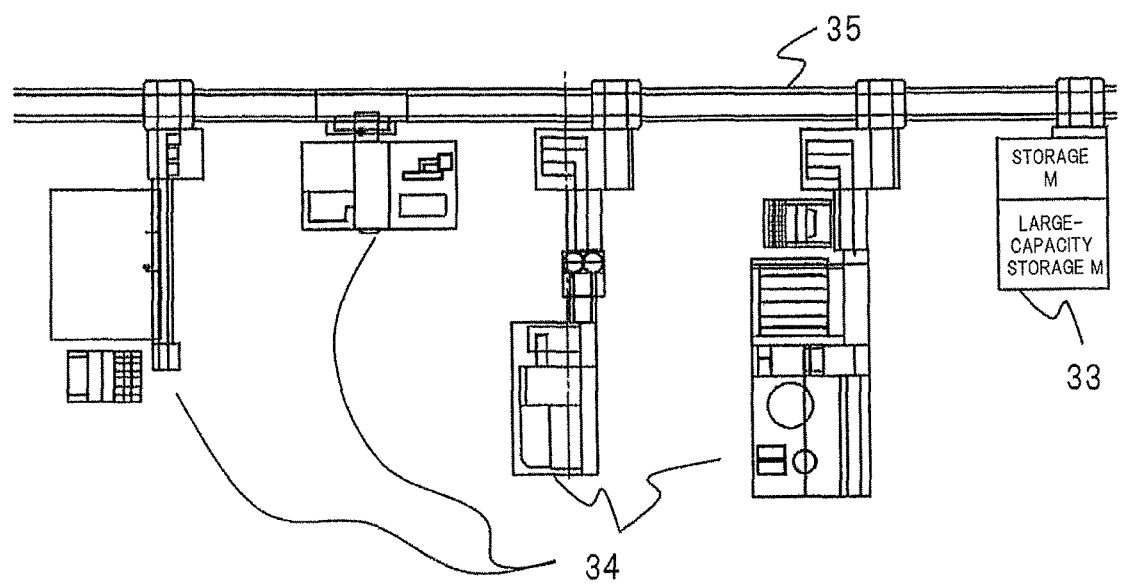
Figure 6:
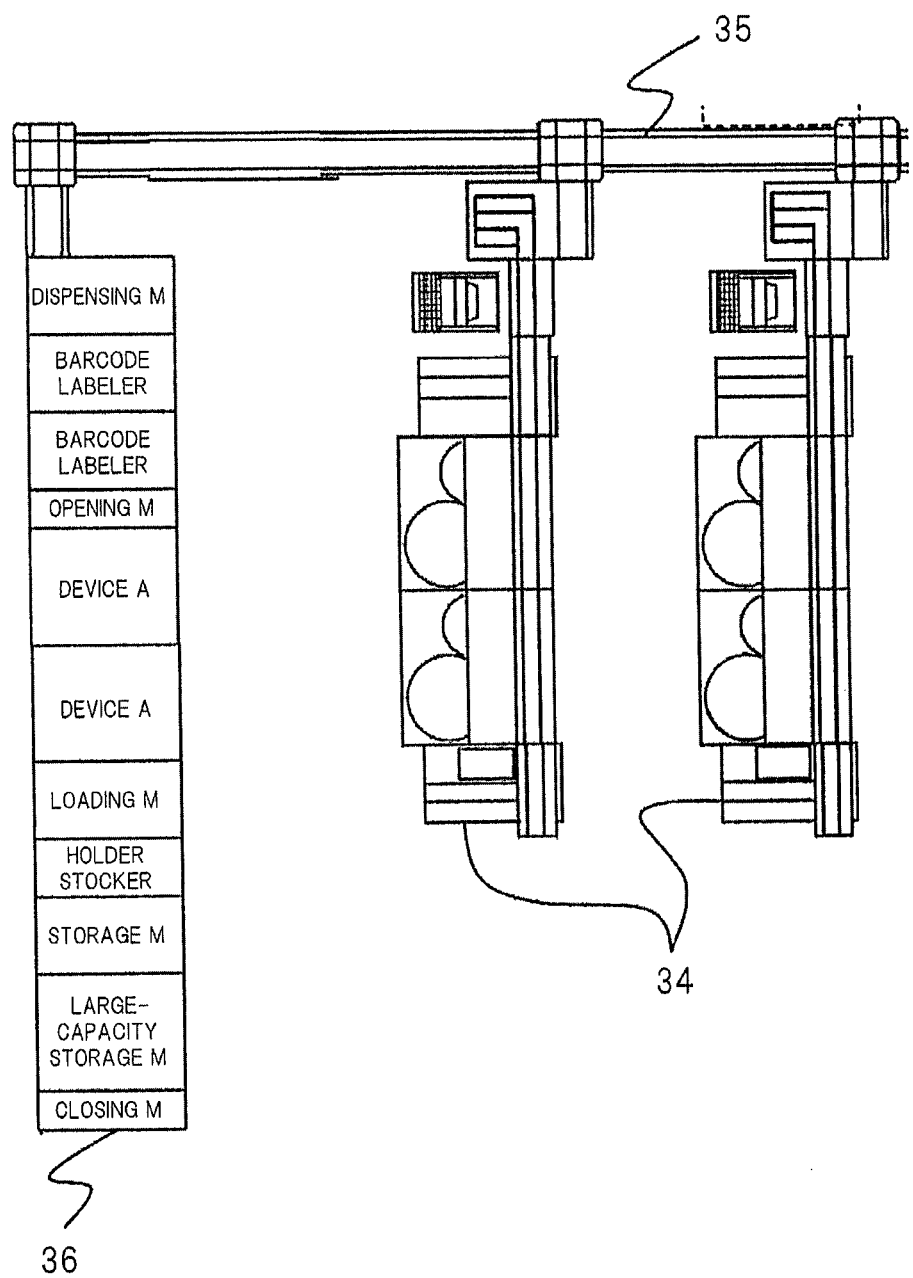
Figure 9:
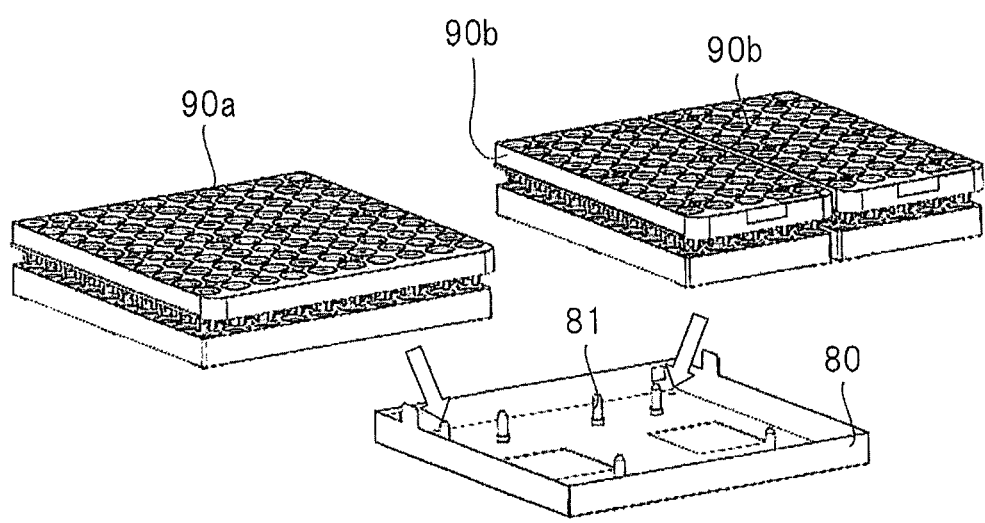

FIGS. 3(a) and 3(b) are diagrams showing the structure of a specimen storage unit in an embodiment of the present invention;

FIGS. 4(a) and 4(b) are diagrams showing details of the operation of a lift mechanism in an embodiment of the present invention;

FIG. 5 is a diagram showing an entire system including the large-capacity specimen storage apparatus and an analyzing apparatus in an embodiment of the present invention;

FIG. 6 is a diagram showing an entire system including the large-capacity specimen storage apparatus and an analyzing apparatus in an embodiment of the present invention;

FIGS. 7(a) and 7(b) are diagrams showing a relation between the lift mechanism and tray shelves in the large-capacity specimen storage apparatus (state in which a tray is held on the lift mechanism) in an embodiment of the present invention;

FIGS. 8(a) and 8(b) are diagrams showing a relation between the lift mechanism and tray shelves in the large-capacity specimen storage apparatus (state in which a tray is held on a tray shelf) in an embodiment of the present invention;

FIG. 9 is a diagram showing an example of installation of a tray on a cassette in an embodiment of the present invention; and FIG. 10 is a diagram showing details of the cassette, a tray for one hundred specimens, and a tray for fifty specimens in an embodiment of the present invention.

DETAILED DESCRIPTION OF PREFERRED EMBODIMENTS

Embodiments of the present invention will be described in detail based on the drawings.

Figure 1:
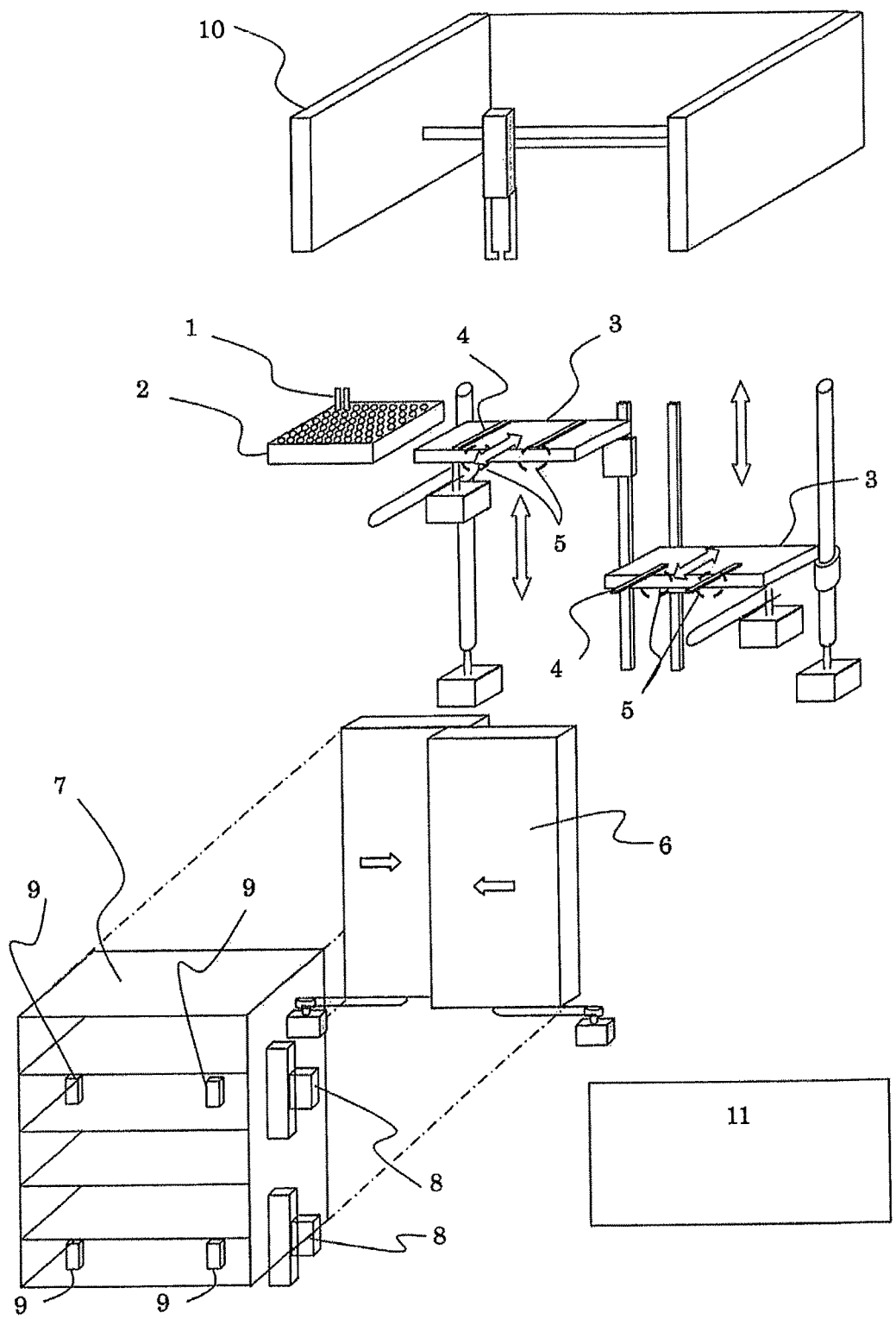
FIG. 1 is a schematic diagram showing an example of the structure of a large-capacity specimen storage apparatus according to an embodiment of the present invention.

FIG. 1 is a schematic diagram showing an example of the structure of a large-capacity specimen storage apparatus according to an embodiment of the present invention.

In FIG. 1, the large-capacity specimen storage apparatus is made up of a specimen conveyor line (not shown) for conveying a specimen installed in a holder for conveying a specimen for which the pre-processing is completed; a lift mechanism 3 capable of driving a specimen tray 2 having specimens 1 installed therein in front-and-back and vertical directions; a specimen chuck mechanism 10 which picks up and transfers the specimen from a specimen acquisition position of the specimen conveyor line to the specimen tray 2 on the lift mechanism 3; a specimen storage unit 7 which receives the specimen tray 2 from the lift mechanism 3, includes hierarchical specimen storage spaces in a vertical direction, and stores a plurality of specimen trays 2 in a lateral direction while keeping them cold; a shutter mechanism 6 which is opened and closed in response to delivery of the specimen tray 2 between the lift mechanism 3 and the specimen storage unit 7; and a control unit 11 which controls each of the mechanisms.

In FIG. 1, the specimen storage unit 7 has five shelves for accommodating specimen trays in the vertical direction, and two specimen trays can be laterally installed on each shelf. Note that the number of specimens required to be stored in the specimen storage unit 7 varies depending on the size of a system to which the specimen storage unit 7 is to be connected. It is desired to provide expandability so that the number of specimens which can be stored in the specimen storage unit 7 can be changed when the system is expanded or reduced or when the operation of the specimen storage unit 7 is changed. For example, a plurality of specimen storage units 7 can be used while being connected in parallel with each other, and the shelf for accommodating the specimen trays in the specimen storage unit 7 may be formed into a cassette shape so as to enable the expansion and reduction of the system.

By drawing each tray out from the specimen storage unit 7 and holding it on the lift mechanism, the specimen chuck mechanism 10 can perform a specimen installing operation on any of two specimen trays on the lift mechanism. A tray to be drawn can be selected from any of the stages. Also, the present embodiment is provided with two lift mechanisms, and the lift mechanisms 3 each include an individual vertical driving mechanism so as to be able to operate independently from each other. Furthermore, each lift mechanism is provided with an arm 4 for mutually transferring the specimen tray 2 between the lift mechanism 3 and the specimen storage unit 7.

Note that FIG. 1 discloses the apparatus structure including two lift mechanisms, but if the driving mechanism itself for vertical driving in the lift mechanism is capable of lateral driving, the structure may be such that one driving mechanism is shared among a plurality of lift mechanisms.

A flow of operation at the time of storing a specimen will be described below.

Examples of structure of a system having the large-capacity specimen storage apparatus in the present invention are shown in FIG. 5 and FIG. 6.

FIG. 5 shows the case in which a plurality of analyzing apparatuses 34 are connected in series to a specimen conveyor line 35 and a large-capacity specimen storage apparatus 33 in the present invention is connected at the lowermost stream part thereof. In the system of FIG. 5, it is often the case that a loading module in which an operator manually loads a specimen or a pre-processing system which performs pre-processing required for specimens is connected to the uppermost stream part of each analyzing apparatus.

When a specimen is loaded, the specimen is mounted on a rack or holder for conveying a specimen, and is conveyed to an optimum analyzing apparatus 34 based on a requested analytical item. The specimen for which measurements of requested analytical items are all completed is conveyed to the specimen storage apparatus 33 in the present invention via the specimen conveyor line 35, is transferred onto a tray, and is stored while keeping it cold in the specimen storage unit of the specimen storage apparatus. Here, memory means in the system stores data as to which position on which tray the specimen has been stored at.

When a request for a retest or additional test on the specimen stored in the specimen storage apparatus 33 is made, the system reads information regarding the tray where the specimen is stored and the position of the tray from the memory means. The specimen is taken out from the position of the specified tray, is again transferred onto a specimen conveyance member such as a rack or holder, and is then conveyed to an optimum analyzing apparatus 34 based on the requested retest or additional test. Here, the specimen conveyor line 35 desirably includes a main line for conveying a specimen from upstream to downstream, a return line for conveying a specimen from downstream to upstream, and a cross line for letting a rack or holder come and go between the main line and the return line. Note that the specimen for which requested analyses at the analyzing apparatus 34 are all completed is again conveyed to the large-capacity specimen storage apparatus 33 and stored in a tray in the apparatus.

On the other hand, FIG. 6 is a diagram showing an example of system structure when a specimen pre-processing system 36 and the analyzing apparatus 34 are connected via the specimen conveyor line 35. In this system, the large-capacity specimen storage apparatus 33 of the present invention is included inside the specimen pre-processing system 36.

In the large-capacity specimen storage apparatus 33, the specimen for which the pre-processing is completed at the specimen pre-processing system 36 is stored. Here, memory means in the system stores data as to which position on which tray the specimen has been stored at. When an analysis request for the stored specimen is made, the system specifies the tray where the specimen is stored and the position of the tray based on the information stored in the memory means, takes out a relevant specimen from the tray, and transfers it onto a rack or holder. The specimen passes through the specimen pre-processing system and is conveyed via the specimen conveyor line 35 to an optimum analyzing apparatus 34, and the requested analysis is performed. The specimen for which the analysis is completed is stored again in the large-capacity specimen storage apparatus 33 in the specimen pre-processing system via the specimen conveyor line 35. In this case, the large-capacity specimen storage apparatus of the present invention is placed at the lowermost stream part of the specimen pre-processing system.

In the case of FIG. 6, a specimen is loaded from a specimen loading apparatus and is conveyed via a main line (not shown) to each processing apparatus for performing necessary pre-processing. If a request for analysis by the analyzing apparatus 34 is already present at this point of time, the specimen is conveyed to the appropriate analyzing apparatus 34 at the time when arriving at a dispensing module at the tail end. On the other hand, if a request for analysis is not present at this point of time, the specimen is stored into the large-capacity specimen storage apparatus via a return line (not shown). When a request for analysis of the stored specimen is made, the system specifies the tray where the specimen is stored and the position of the tray based on the stored information, takes out the relevant specimen from the tray, and transfers the specimen onto a rack or holder. The specimen passes through the specimen pre-processing system and is conveyed via the specimen conveyor line 35 to an optimum analyzing apparatus 34, and the requested analysis is performed. The specimen for which the analysis is completed is stored again into the large-capacity specimen storage apparatus in the specimen pre-processing system via the specimen conveyor line 35.

In the case of FIG. 5 and FIG. 6, the specimen that is taken out from the large-capacity specimen storage apparatus 33, is subjected to analysis processing, and is then stored again in the large-capacity specimen storage apparatus 33 is desirably stored at the same position as the position where the specimen is stored before being taken out.

Figure 2:
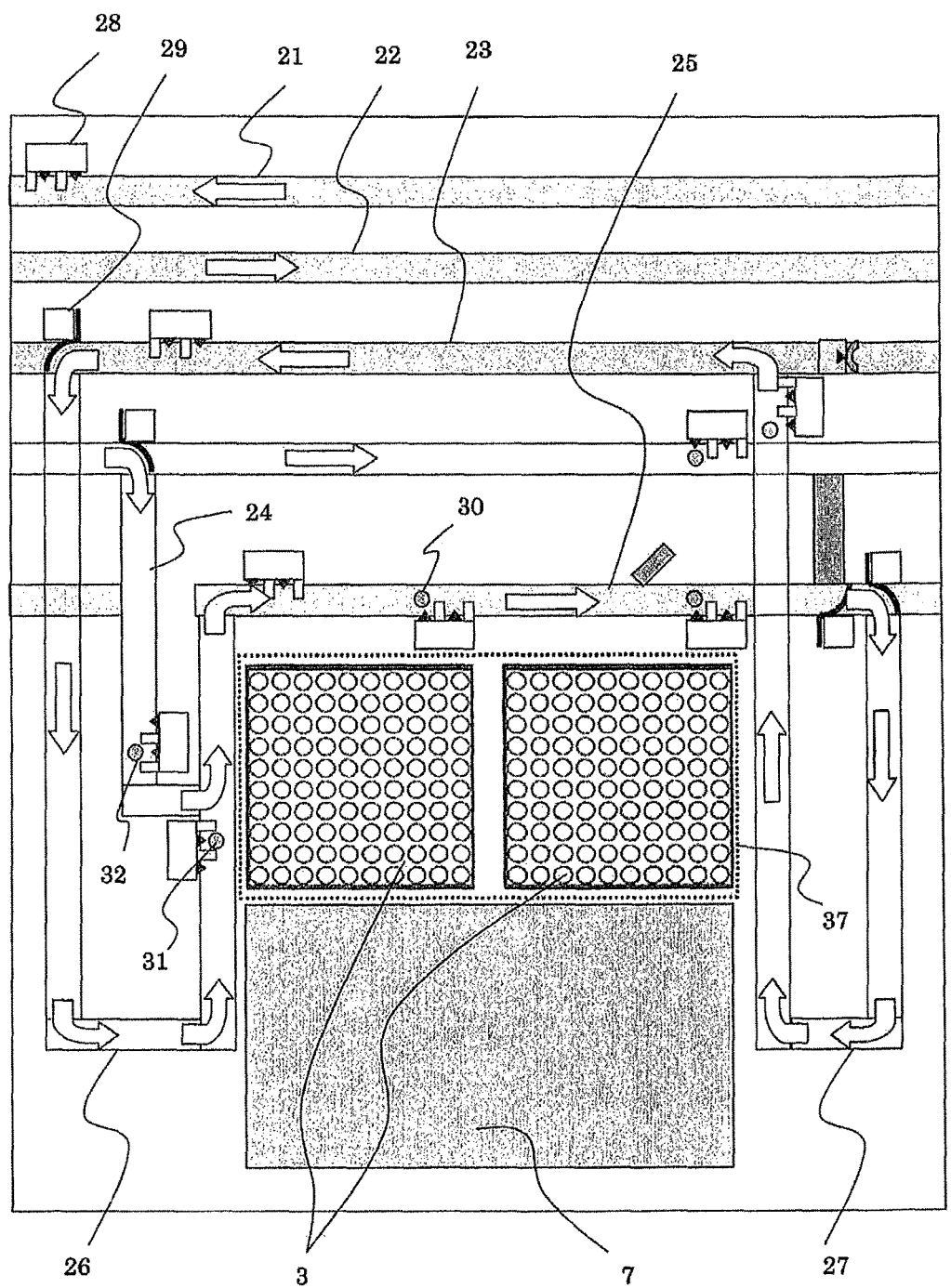
FIG. 2 is a diagram showing the structure of the large-capacity specimen storage apparatus and an example of the structure of a specimen conveyor line in the apparatus in an embodiment of the present invention.

For the description of the structure of the large-capacity specimen storage apparatus 33, the structure of the large-capacity specimen storage apparatus and an example of the structure of the specimen conveyor line in the apparatus are shown in FIG. 2.

FIG. 2 shows the structure made up of a specimen storage unit 7 formed in multiple stages each capable of accommodating two trays, a standby position 37 indicated by broken lines and corresponding to a position where a conveyed specimen is transferred onto a tray taken out from the specimen storage unit 7, a plurality of conveyor lines 24 for conveying the specimen to be transferred onto the tray, a stopper for stopping the specimen to be processed at a predetermined position, and an RFID read antenna. Note that the operator needs to install an empty specimen tray on each tier of the specimen storage unit 7 before operating the apparatus. For this reason, the specimen storage unit 7 is configured to have an openable and closable front surface, so that the operator can easily take in and out the specimen tray.

The specimen installed on a holder for conveying a specimen for which pre-processing or analysis is completed is supplied by the specimen holder conveyor line 24 from an apparatus adjacent on an upstream side to the large-capacity specimen storage apparatus. For the specimen supplied into the large-capacity specimen storage apparatus, a specimen ID is read at a holder RFID read position 32, and a predetermined amount thereof can be buffered by a stopper provided at an RFID read position. The specimen ID information read at the holder RFID read position is stored in a memory device described further below.

In the period when the specimen moves from the holder RFID read position 32 to a specimen chuck position 30, the lift mechanism 3 moves to take out the specimen tray 2 having an empty position from the specimen trays accommodated in a cooling box of the specimen storage unit 7, and carries the specimen tray 2 to a standby position where the specimen 1 picked up by the chuck mechanism 10 can be received.

The specimen tray 2 has an identifier (for example, an RFID tag, a barcode label, etc.) including identification information by which each specimen tray 2 can be identified. By providing a reader (for example, an RFID tag reader, a barcode reader, etc.) which can read this identifier to the lift mechanism or the like, the specimen tray 2 which is storing a specimen can be identified on an apparatus side. The identification information of the specimen tray 2 read this time is stored in the memory device.

When the specimen arrives at the specimen chuck position 30 on a main line 25, the large-capacity specimen storage apparatus recognizes the arrival by a specimen detection sensor on the main line 25, picks up the specimen by the chuck mechanism 10, and then transfers the specimen onto an empty position of the specimen tray 2 on the lift mechanism 3. The chuck mechanism is attached to a driving mechanism such as an XYZ mechanism or a rotatable arm so as to be able to transfer a specimen to any position. Here, position information as to which position the specimen has been transferred to by the driving mechanism is stored in the memory device.

The memory device stores the specimen ID information read at the holder RFID read position 32, the identification information of the specimen tray read by the reader, and information about the position on the specimen tray where the specimen is stored by the chuck mechanism in a specimen storage operation by the specimen chuck mechanism, in association with each other. Consequently, the specimen stored in the specimen storage unit 7 can be appropriately managed, and it becomes possible to handle a request for a retest or additional test.

At the standby position, one tray is held on each of two lift mechanisms arranged in a lateral direction, and the chuck mechanism 10 can access any of the specimen trays 2. Consequently, when one specimen tray 2 is about to become full, the other lift mechanism 3 can prepare an empty specimen tray 2 in the cooling box as a new specimen tray to be used next before the tray actually becomes full. Therefore, the storage processing can be continued without time loss.

When one specimen tray 2 becomes full, the chuck mechanism continues a specimen transfer operation to the new specimen tray other than the specimen tray that has become full. The lift mechanism 3 holding the specimen tray 2 that has become full ascends or descends in order to access a tier where the specimen tray 2 that has become full has been initially accommodated. The shutter mechanism 6 of the specimen storage unit 7 starts an opening operation simultaneously with the start of the ascending or descending operation of the lift mechanism 3.

When it is confirmed that the shutter mechanism 6 has been completely opened, the lift mechanism 3 extends the arm 4 to accommodate the specimen tray 2 into the specimen storage unit 7. Then, when it is confirmed that the arm 4 of the lift mechanism 3 is out of the specimen storage unit 7, the shutter mechanism 6 performs a closing operation. In order to keep a low temperature inside the specimen storage unit 7, the shutter mechanism 6 is always closed when a motion of accommodating or taking out the specimen tray 2 is not performed.

Note that an empty specimen conveyance holder from which the specimen has been taken out at the specimen chuck position 30 in order to transfer the specimen onto the specimen tray 2 is conveyed via an empty holder discharge line 27 to an empty holder conveyor line 23, and it is reused for the conveyance of another specimen.

Next, a flow of operation when a request for a retest or additional test on the specimen stored in the specimen storage unit 7 is made will be described below.

When a doctor determines that a retest or additional test is necessary in overall consideration of all analysis results and previous measurement values regarding the specimen and patient's condition, the doctor make a request for analysis from, an upper host system. Alternatively, it is also possible to make contact with an operator and make a request for analysis from an input device of the specimen conveyor system. When a request for a retest or a request for an additional test described above is made, the control unit 11 searches information stored inside the memory device (not shown) for a specimen ID of the requested specimen and storage position information stored in association with the specimen having the specimen ID.

When the relevant specimen 1 is present on the specimen tray 2 which is currently held on the lift mechanism 3 and is being subjected to storage processing, the process of transferring the specimen onto the specimen tray by the chuck mechanism is temporarily stopped. In order to convey the specimen 1 to the analyzing apparatus for performing the requested test, a conveyance member which conveys the specimen, namely, a specimen holder or specimen rack to another apparatus is prepared, and the specimen is transferred by the chuck mechanism onto the conveyance member.

When the specimen 1 on which a request for a retest or additional test is made is not on the tray which is currently held on the lift mechanism 3, an operation of taking out a predetermined specimen tray is performed by using the lift mechanism 3 which does not currently perform a specimen transfer operation. When another specimen tray is held on the lift mechanism 3, this specimen tray is first required to be accommodated in the specimen storage unit 7, and therefore the lift mechanism is caused to ascend or descend so as to access the tier where the specimen tray 2 has been initially accommodated.

The shutter mechanism 6 starts an opening operation simultaneously with the start of an ascending or descending operation of the lift mechanism 3. When it is confirmed that the shutter mechanism 6 is fully opened, the lift mechanism 3 extends the arm 4 to accommodate the specimen tray 2 currently held on the lift mechanism 3 into the specimen storage unit 7.

When accommodation of the tray 2 is completed and it is confirmed that the arm 4 is out of the specimen storage unit 7, the lift mechanism 3 ascends or descends toward the tier where the specimen tray 2 in which the specimen 1 for which the analysis is requested is stored is accommodated. Then, after extending the arm 4 to take out the desired specimen tray 2 accommodated in the specimen storage unit 7, the lift mechanism ascends or descends to the standby position to exchange the specimen 1 with the chuck mechanism 10.

The shutter mechanism 6 performs a closing operation when it is confirmed that the arm 4 of the lift mechanism 3 is out of the specimen storage unit 7. When the lift mechanism 3 arrives at the standby position, the chuck mechanism 10 takes out the specimen 1 from the specimen tray 2 based on the information about the position where the relevant specimen 1 is held, and transfers the specimen onto an empty specimen conveyance holder supplied from an empty holder supply line 26 and standing by at the specimen chuck position 30 on the main line 25. The specimen 1 installed on the specimen conveyance holder is conveyed through the main line 25 to an analyzing apparatus where a retest or additional test is performed.

In the present embodiment, the system in which the specimen is mounted on a holder and conveyed via a belt conveyer is employed for the transfer of the specimen to and from the specimen storage apparatus and the analyzing apparatus, but the present invention is not limited to this system. For example, a system in which the specimen is chucked and conveyed by the arm mechanism to an arbitrary analyzing apparatus may be employed.

With these structures, when a request for a retest or additional test is made, the specimen can be automatically taken out by making a search for the specimen tray 2 having the relevant specimen stored therein and the position of the specimen on the specimen tray. Therefore, a retest or additional test can be automatically performed without the actions of an operator.

Next, the structure of the specimen storage unit 7 will be described.

First Embodiment

The structure of the specimen storage unit 7 is shown in FIG. 3(a).

In the specimen storage unit of FIG. 3, the specimen storage unit has five shelves, and one shelf can accommodate two specimen trays.

The specimen storage unit 7 circulates cooling air cooled by a cooling unit 8 by a blower fan 9, thereby uniformly keeping low temperature inside the specimen storage unit 7. A flow of the cooling air in the specimen storage unit 7 is indicated by an arrow 13 in FIG. 3(a). Consequently, the specimen can be stored under the uniform low temperature condition even if the specimen is stored at any position in the specimen storage unit configured in multiple stages.

Also, since the inside of the specimen storage unit is kept cold and the shutter mechanism or the like is opened and closed when a specimen tray present therein is taken out, there is a possibility of occurrence of dew condensation water in the storage unit. If dew condensation water is accumulated inside the specimen storage unit, not only there is a possibility of proliferation of various bacteria, but the dew condensation water may be attached to a specimen container to damage a barcode affixed to the specimen container and the specimen may be diluted. Thus, a path 14 for dew condensation water is provided in order to prevent dew condensation water from being accumulated around or dripping onto the specimen. Dew condensation water is accumulated in a drain 12 via the path 14 and is discarded by the operator.

When dew condensation water is accumulated on a lower surface of a shelf serving as the specimen storage part of the specimen storage unit 7, there is a possibility that the dew condensation water drips onto a specimen container stored on a stage below it. Thus, in order to avoid this situation, the lower surface of the shelf may be configured to be tilted so that dew condensation water is collected in the drain 12.

A flow of operation at the time of taking out a specimen tray by the lift mechanism 3 will be described with reference to a left column of FIG. 4(a).

The lift mechanism 3 ascends or descends to an arbitrary tier where the tray 2 to be taken out is accommodated, and stops at a position lower than a specimen tray shelf 15 where the specimen tray 2 is held in the specimen storage unit 7 (first stage in the left column of FIG. 4(a)).

After it is confirmed that the shutter mechanism is opened, the arm 4 is extended until the tip of the arm 4 reaches the position below the specimen tray 2 (second stage in the left column of FIG. 4(a)).

When it is confirmed that the arm 4 has been fully extended, the lift mechanism 3 is caused to ascend to a position slightly higher than the specimen tray shelf 15. Consequently, the specimen held on the specimen tray shelf 15 is held by the arm 4 of the lift mechanism 3 (third stage in the left column of FIG. 4(a)).

The arm 4 is retracted and the lift mechanism is caused to ascend or descend to a standby position where the chuck mechanism 10 can access the specimen (fourth stage in the left column of FIG. 4(a)).

A flow of operation of the lift mechanism 3 at the time of accommodating a specimen tray will be described with reference to a right column of FIG. 4(a).

The lift mechanism 3 ascends or descends from the standby position where the chuck mechanism 10 accesses the specimen to a tier where the specimen tray 2 currently held by the lift mechanism 3 has been initially accommodated, and stops at a position higher than the specimen tray shelf (first stage in the right column of FIG. 4(a)).

After it is confirmed that the shutter mechanism is opened, the arm 4 is extended to convey the specimen tray 2 to the inside of the specimen storage unit 7 (second stage in the right column of FIG. 4(*a*)).

After the arm 4 is fully extended and it is confirmed that the specimen tray 2 has been conveyed to an appropriate position of the specimen tray shelf, the arm 4 is caused to descend to a position slightly lower than the specimen tray shelf (third stage in the right column of FIG. 4(*a*)).

Then, the arm 4 is retracted to make a transition to the next operation (fourth stage in the right column of FIG. 4(*a*)).

With this operation flow, the positional adjustment in height between the lift mechanism 3 and the specimen storage unit 7 does not require the strict adjustment, so that the structure can be simplified.

As a structure for taking out a specimen tray, the lift mechanism has a projection part for catching the specimen tray 2. Details of the shelves of the specimen storage unit 7 and the structure of the lift mechanism will be described with reference to FIG. 7 and FIG. 8. Note that FIG. 7 and FIG. 8 correspond to diagrams of the lift mechanism and the shelves of the specimen storage unit viewed from above (FIG. 7(*a*)) and laterally (FIG. 7(*b*)), and each shows the lift mechanism on an upper side of the drawing and a shelf part of the specimen storage unit on a lower side thereof.

Figure 7:
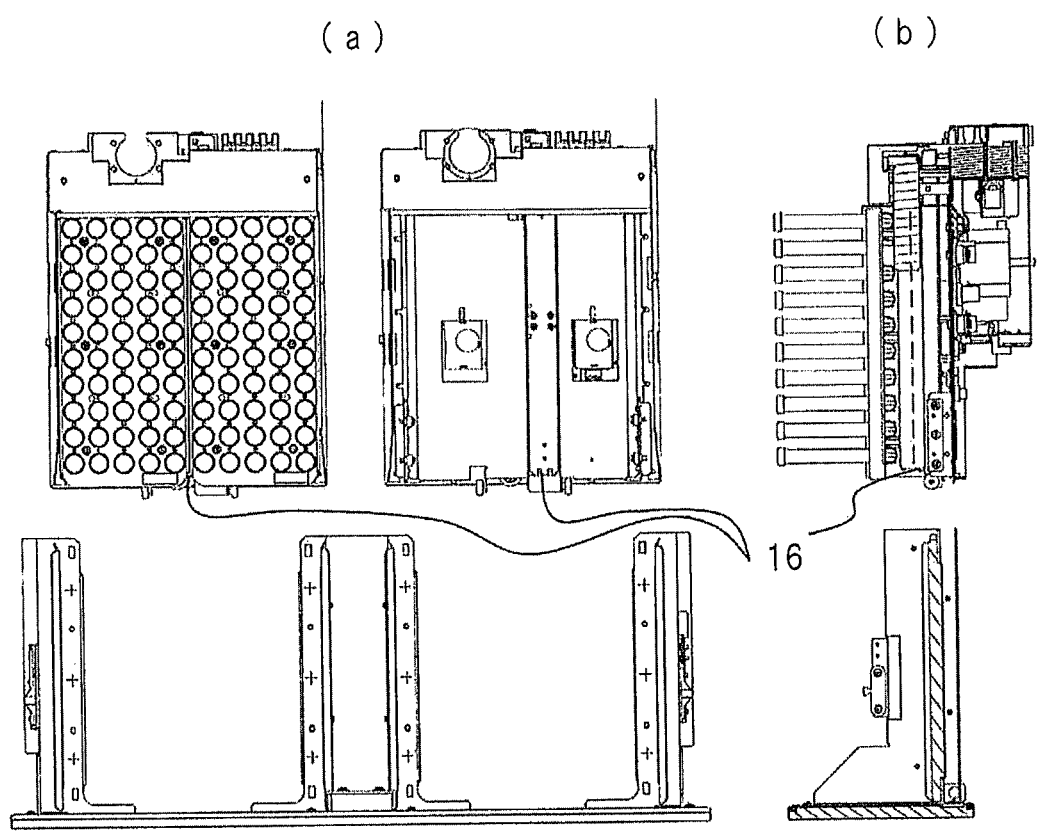

FIG. 7 shows the state in which trays are held on the lift mechanism. A tray moves onto the lift mechanism by inserting the arm of the lift mechanism into the specimen storage unit. At the tip of the arm, a tray drawing projection 16 for drawing the tray in the specimen storage unit onto the lift mechanism is provided. At the time of the operation of taking out a specimen tray in FIG. 4(*a*), this projection passes through a lower side of the tray and catches an end of the tray, thereby drawing the tray onto the lift. Thus, in order to prevent the projection from being caught by the tray itself at the time of the operation of taking out the tray, the projection is formed to have a size shorter than the length by which the lift mechanism ascends before and after the operation of taking out the tray. On the other hand, in the shelves of the specimen storage unit, a hollow area which allows the entry of the lift mechanism is formed at a center part so as to enable the shelf to hold the specimen tray and enable the lift mechanism to perform the taking-out operation. The tray drawing projection acts on a tray in this hollow area.

FIG. 8 shows the state in which a tray is being returned from the lift mechanism to the shelves of the specimen storage unit. The lift mechanism holding a tray extends the arm to return a tray to an empty position in the specimen storage unit. Here, a tray pushing projection 17 for pushing a tray is provided on the arm. With the tray pushing projection, the tray is accommodated at a predetermined position in the shelves of the specimen storage unit.

Note that the specimen storage unit 7 of the specimen storage apparatus may be configured so that only this part can be carried separately from the overall system. For example, by providing a caster on a lower part of the specimen storage unit 7 and separating the specimen storage unit 7 from the system after the end of analysis, the specimen storage unit 7 can be easily carried to any location. In this manner, specimen trays can be easily moved in a laboratory where the trays in the specimen storage unit 7 are stored in another location such as a refrigerator.

The mechanisms described in the present embodiment are shown merely by way of example, and may be achieved by another means. Also, though the case of motor driving has been described in the present embodiment, another driving means such as air driving with an air syringe may be used.

Furthermore, the specimen storage apparatus in the present invention is not limited to the structure of FIG. 1, and three or more lift mechanisms may be provided. In this case, three or more specimen trays can be arranged on standby on the lift mechanism in the same orientation as that of the lift mechanism, so that the chuck mechanism 10 can perform a specimen installing operation for these specimen trays.

Still further, the shelves for accommodating specimen trays provided in the specimen storage unit 7 may be configured to be driven vertically. In this case, it is desired that a conveyor apparatus capable of moving only in a front-and-back direction holds the specimen tray 2 at the standby position in place of the lift mechanism. If a plurality of the conveyor apparatuses are arranged next to each other, when one specimen tray 2 becomes full, the shelves of the specimen storage unit 7 are driven and an optimum accommodation shelf moves to a position of receiving a specimen tray. Then, the conveyor apparatus is driven to push the tray forward, and the specimen tray can be accommodated at an appropriate position in the specimen storage unit 7. Still further, since a plurality of conveyor apparatuses are provided, when one specimen tray becomes full and the above-described accommodating operation is being performed, a specimen storage operation can be performed on another specimen tray, so that specimen storage control can be successively performed.

Second Embodiment

The structure of the specimen storage unit 7 is shown in FIG. 3(*b*).

In the specimen storage unit of FIG. 3, the specimen storage unit has five shelves, and one shelf can accommodate two specimen trays.

A cooling unit is disposed on a lower surface of the specimen storage unit 7, and the cooling unit has a cooling surface configured to make a close contact with the bottom surface of the specimen storage unit. When the specimen storage apparatus is activated, the cooling unit is simultaneously activated to cool the bottom surface of the specimen storage unit. For the bottom surface and wall surfaces of the specimen storage unit, a heat conductive member such as aluminum or copper is used, so that coldness from the bottom surface is transmitted to the wall surfaces and the entire wall surfaces of the storage unit are cooled. The inside of the storage chamber is kept cold by heat dissipation of the cooled wall surfaces.

Although the case where the cooling unit is disposed on the lower surface of the specimen storage unit is described, the cooling unit may be disposed on a side surface or upper surface of the specimen storage unit.

For dew condensation water, a path (not shown) for dew condensation water is provided like the first embodiment. Alternatively, a water-absorbing member may be fixed onto the upper surface.

Next, a flow of operation of the lift mechanism 3 at the time of taking out a cassette will be described with reference to a left column of FIG. 4(*b*).

The lift mechanism 3 ascends or descends to an arbitrary tier where the tray 2 to be taken out is accommodated, and stops at a position lower than the specimen tray shelf 15 where the specimen tray 2 is held in the specimen storage unit 7 (first stage in the left column of FIG. 4(*b*)).

After it is confirmed that the shutter mechanism is opened, the arm 4 is extended until the tip of the arm 4 reaches the position below the specimen tray 2 (second stage in the left column of FIG. 4(b)).

When it is confirmed that the arm 4 has been fully extended, the lift mechanism 3 is caused to ascend to the same height as that of the specimen tray shelf 15 (third stage in the left column of FIG. 4(b)).

The arm 4 is retracted to cause the lift mechanism to ascend or descend to a standby position where the chuck mechanism 10 can access the specimen (fourth stage in the left column of FIG. 4(b)).

A flow of operation of the lift mechanism 3 at the time of accommodating a specimen tray will be described with reference to a right column of FIG. 4(b).

The lift mechanism 3 ascends or descends from the standby position where the chuck mechanism 10 accesses the specimen to the tier where the specimen tray 2 currently held by the lift mechanism 3 has been initially accommodated, and stops at the same height position as the specimen tray shelf (first stage in the right column of FIG. 4(b)).

After it is confirmed that the shutter mechanism is opened, the arm 4 is extended to convey the specimen tray 2 to the inside of the specimen storage unit 7 (second stage in the right column of FIG. 4(b)).

After the arm 4 is fully extended and it is confirmed that the specimen tray 2 has been conveyed to an appropriate position of the specimen tray shelf, the arm 4 is caused to descend to a position slightly lower than the specimen tray shelf (third stage in the right column of FIG. 4(b)).

Then, the arm 4 is retracted to make a transition to the next operation (fourth stage in the right column of FIG. 4(b)).

In this operation flow, since the specimen tray can be drawn without being lifted on the tray shelf, there is no need for unnecessarily increasing the height of the storage unit. Also, since the operation time can be reduced by the time for the lifting operation, throughput can be improved.

As a structure for taking out a specimen tray, the lift mechanism has a projection part for catching the specimen tray 2 and a tilted part 38 for receiving a tray. By providing the tilted part 38 for receiving a tray, a minute difference in height of the stop position of the lift mechanism with respect to the tray shelf is compensated for without strict positional adjustment in height, and the specimen tray can be delivered without being stuck at the time of the delivery of the specimen tray between the lift mechanism and the tray shelf.

Third Embodiment

The structure of a cassette is shown in FIG. 9 and FIG. 10. By using the cassette, the specimen tray can be expanded.

A cassette 80 has six projecting parts 81 on an upper surface thereof as shown in FIG. 9 and FIG. 10. For the cassette 80, a tray 90a has six dent parts 91a on a bottom surface at positions opposed to the projecting parts 81, and an operator fits the dent parts 91a of the tray 90a to the projecting parts 81 of the cassette 80. By employing the fit-in type, the tray 90a can be installed every time without positional error. At this time, if the tray 90a is oriented in a wrong direction, the positions of the projecting parts 81 and the dent parts 91a do not match each other, and the tray 90a cannot be installed.

Also, for example, when a tray 90b capable of having fifty specimens mounted thereon is desired to be installed, three dent parts 91b on the bottom surface of the tray 90b are configured to be able to fit to three projecting parts 81 opposed thereto out of the six projecting parts 81 on the upper surface of the cassette 80, and two trays 90b can be installed. Also in the tray 90b, because of the positions of the projecting parts and the dent parts, the tray oriented in a wrong direction cannot be installed.

Still further, the tray 90b is a compatible tray which can be used also in a specimen storage apparatus and a specimen loading apparatus of a conventional specimen test automation system other than the specification of the specimen storage apparatus described above.

Furthermore, expansion and reduction of trays such as a tray for installing twenty five specimens and a tray for installing two hundred specimens are possible by increasing the dent parts of the tray and the projecting parts of the cassette.

Here, when the tray 90b is to be installed without the presence of the cassette 80, since the storage unit has a shape that can support only one side of the tray 90b, the tray 90b is dropped off. Thus, when installing the tray 90b, it is inevitable that a tray installing part of the storage unit has a complicated structure. This problem can be solved by using the cassette 80.

DESCRIPTION OF REFERENCE CHARACTERS

1 . . . specimen
2 . . . specimen tray
3 . . . lift mechanism
4 . . . arm
5 . . . RFID reader
6 . . . shutter mechanism
7 . . . specimen storage unit
8 . . . cooling unit
9 . . . blower fan
10 . . . specimen chuck mechanism
11 . . . control unit
12 . . . drain
13 . . . air flow
14 . . . path for dew condensation water
15 . . . specimen tray shelf
16 . . . tray drawing projection
17 . . . tray pushing projection
21 . . . return line
22 . . . empty holder return line
23 . . . empty holder conveyor line
24 . . . specimen holder conveyor line
25 . . . main line
26 . . . empty holder supply line
27 . . . empty holder discharge line
28 . . . empty holder stopper
29 . . . branch mechanism
30 . . . specimen chuck position
31 . . . RFID read position for empty holder
32 . . . RFID read position for specimen holder
33 . . . large-capacity specimen storage apparatus
34 . . . analyzing apparatus
35 . . . specimen conveyor line
36 . . . specimen pre-processing system
37 . . . standby position
38 . . . tilted part for receiving a tray
80 . . . tray installation cassette
81 . . . projecting part
90a . . . specimen tray (for installing one hundred specimens)
90b . . . specimen tray (for installing fifty specimens)
91a . . . dent part (specimen tray (for installing one hundred specimens))

91b . . . dent part (specimen tray (for installing fifty specimens))

The invention claimed is:
1. A specimen storage apparatus comprising:
a specimen storage unit which has plurality of accommodation positions where a plurality of trays each holding one or more of a plurality of specimens can be individually accommodated;
a standby position where at least two of the trays holding the specimens are on standby;
at least two lift mechanisms to individually transfer the trays between the accommodation positions of the specimen storage unit and the standby position;
a specimen chuck mechanism to pick up and transfer individual ones of the specimens between a specimen acquisition position and ones of the specimen trays held on the lift mechanisms at the standby position; and
control means which controls an operation of each of the lift mechanisms and the specimen chuck mechanism,
wherein, when a retest is requested for a first one of the specimens, the control means determines whether the first one of the specimens is present on a first one of the trays which is currently held by one of the lift mechanisms,
when the first one of the specimens is present on the first one of the trays which is currently held by one of the lift mechanisms, the control means controls the specimen chuck mechanism to transfer the first one of the specimens to the specimen acquisition position, and
when the first one of the specimens is not present on the first one of the trays which is currently held by one of the lift mechanisms, the control means interrupts the one of the lift mechanisms to place a second one of the trays currently held thereon at one of the accommodating positions in the specimen storage unit, take out the first one of the trays on which the first one of the specimens is held from the specimen storage unit, transfer the first one of the trays to the standby position, and control the specimen chuck mechanism to transfer the first one of the specimens to the specimen acquisition position.

2. The specimen storage apparatus according to claim 1, wherein each of the lift mechanisms includes a horizontal driving means which independently drives ones of the plurality of trays at the standby position in a horizontal direction.

3. The specimen storage apparatus according to claim 1, wherein the specimen storage unit has a cooling unit and one or more blower fans for circulating cooling air therein.

4. The specimen storage apparatus according to claim 1, wherein each of the lift mechanisms includes vertical driving means which independently drives ones of the plurality of trays at the standby position in a vertical direction and horizontal driving means which independently drives ones the plurality of trays at the standby position in a horizontal direction.

5. The specimen storage apparatus according to claim 3, wherein the specimen storage unit has an opening through which the trays are transferred by the lift mechanisms from the accommodation positions, and
wherein opening and closing means which closes the opening and opens the opening when the trays are transferred.

6. The specimen storage apparatus according to claim 1, wherein the specimen storage unit includes an opening through which ones of the trays can be taken out by an operator and opening and closing means for the opening.

7. A specimen processing system comprising:
a specimen storage apparatus;
an analyzing apparatus which performs an analysis of one or more of a plurality of specimens;
a conveyor apparatus which conveys the specimens between the specimen storage apparatus and the analyzing apparatus; and
a control device which controls the specimen storage apparatus, the analyzing apparatus, and the conveyor apparatus,
wherein the specimen storage apparatus includes:
a specimen storage unit which has a plurality of accommodation positions where a plurality of trays each holding a plurality of specimens can be individually accommodated;
a standby position where at least two of the trays holding the specimens are on standby;
at least two lift mechanisms to individually transfer the trays between the accommodation positions of the specimen storage unit and the standby position;
a specimen chuck mechanism to pick up and transfer individual ones of the specimens between a specimen acquisition position on the conveyor apparatus and ones of the specimen trays held on the lift mechanisms at the standby position; and
control means which controls an operation of each of the lift mechanisms and the specimen chuck mechanism,
wherein, when a retest is requested for a first one of the specimens, the control means determines whether the first one of the specimens is present on a first one of the trays which is currently held by one of the lift mechanisms,
when the first one of the specimens is present on the first one of the trays which is currently held by one of the lift mechanisms, the control means controls the specimen chuck mechanism to transfer the first one of the specimens to the specimen acquisition position, and
when the first one of the specimens is not present on the first one of the trays which is currently held by one of the lift mechanisms, the control means interrupts the one of the lift mechanisms to place a second one of the trays currently held thereon at one of the accommodating positions in the specimen storage unit, take out the first one of the trays on which the first one of the specimens is held from the specimen storage unit, transfer the first one of the trays to the standby position, and control the specimen chuck mechanism to transfer the first one of the specimens to the specimen acquisition position.

8. The specimen processing system according to claim 7, wherein the conveyor apparatus includes an accumulating unit which accumulates empty specimen conveyance members and a conveyor line for conveying the specimen conveyance members holding the specimens to the analyzing apparatus, and
when a request for analysis of one of the specimens stored in the specimen storage apparatus is received by the control device, the accumulating unit supplies one of the empty specimen conveyance members to the specimen storage apparatus.

9. A method of controlling a specimen storage apparatus which includes a specimen storage unit which has a plurality of accommodation positions where a plurality of trays each holding one or more of a plurality of specimens can be individually accommodated, a standby position where at least two of the trays holding the specimens are on standby, at least two lift mechanisms to individually transfer the trays between the specimen storage unit and the standby position, and a specimen chuck mechanism to pick up and transfer individual ones of the specimens between a specimen acquisition position and ones of the specimen trays held on the lift mechanisms at the standby position, the method comprising:

individually transferring the trays between the accommodation positions and the standby position with the lift mechanisms;

when a retest is requested for a first one of the specimens, determining whether the first one of the specimens is present on a first one of the trays which is currently held by one of the lift mechanisms;

when the first one of the specimens is present on the first one of the trays which is currently held by one of the lift mechanisms, controlling the specimen chuck mechanism to transfer the first one of the specimens to the specimen acquisition position; and when the first one of the specimens is not present on the first one of the trays which is currently held by one of the lift mechanisms, interrupting the one of the lift mechanisms to place a second one of the trays currently held thereon at one of the accommodating positions in the specimen storage unit, take out the one of the trays on which the one of the specimens is held from the specimen storage unit, transfer the one of the trays to the standby position, and transfer the one of the specimens to the specimen acquisition position with the specimen chuck mechanism.

10. The specimen storage apparatus according to claim 1, wherein each of the trays includes a plurality of holes in which the specimens are held, wherein each of the trays is respectively provided in one of a plurality of tray installation cassettes, and wherein the lift mechanisms can individually transfer the tray installation cassettes between the accommodation positions and the standby position.

11. The specimen storage apparatus according to claim 10, wherein each of the tray installation cassettes has two or more projecting parts on an upper surface of the cassette, wherein each of the specimen trays has at least two or more dent parts on a lower surface thereof so as to be opposed to the projecting parts of the tray installation cassettes, and wherein ones of the trays can be installed onto ones of the cassettes by positioning the projecting parts and the dent parts.

12. The specimen storage apparatus according to claim 11, wherein plural ones of the trays can be installed onto one of said tray installation cassettes.

13. The specimen storage apparatus according to claim 10, wherein the specimen storage unit includes a first extraction port through which an operator takes in and out the specimen trays and a second extraction port through which the lift mechanisms transfer the specimen trays in and out.

14. The specimen storage apparatus according to claim 13, wherein, when the operator takes in and out the specimen trays, the specimen trays are taken into and out of the tray installation cassettes through the first extraction port, and when the lift mechanisms take the specimen trays in and out, the tray installation cassettes having the specimen trays mounted thereon are integrally taken in and out through the second extraction port.

* * * * *